(12) United States Patent
Villongco et al.

(10) Patent No.: US 12,290,369 B2
(45) Date of Patent: May 6, 2025

(54) AUTOMATIC FIBRILLATION CLASSIFICATION AND IDENTIFICATION OF FIBRILLATION EPOCHS

(71) Applicant: The Vektor Group Inc., San Diego, CA (US)

(72) Inventors: Christopher J. T. Villongco, Roswell, GA (US); Christian David Marton, Jersey City, NJ (US)

(73) Assignee: VEKTOR MEDICAL, INC., Carlsbad, CA (US)

( * ) Notice: Subject to any disclaimer, the term of this patent is extended or adjusted under 35 U.S.C. 154(b) by 0 days.

(21) Appl. No.: 18/630,900

(22) Filed: Apr. 9, 2024

(65) Prior Publication Data

US 2024/0252094 A1  Aug. 1, 2024

Related U.S. Application Data

(63) Continuation of application No. PCT/US2023/072854, filed on Aug. 24, 2023.
(Continued)

(51) Int. Cl.
*A61B 5/361* (2021.01)
*A61B 5/00* (2006.01)
(Continued)

(52) U.S. Cl.
CPC .............. *A61B 5/361* (2021.01); *A61B 5/355* (2021.01); *A61B 5/36* (2021.01); *A61B 5/367* (2021.01);
(Continued)

(58) Field of Classification Search
None
See application file for complete search history.

(56) References Cited

U.S. PATENT DOCUMENTS

2019/0059763 A1* 2/2019 Shakur ................... G16H 40/67
2019/0082988 A1* 3/2019 Datta ...................... A61B 5/366
(Continued)

FOREIGN PATENT DOCUMENTS

WO    2022034045 A1    2/2022

OTHER PUBLICATIONS

Baek, Y.S., et al., "A new deep learning algorithm of 12-lead electrocardiogram for identifying atrial fibrillation during sinus rhythm," Scientific Reports, Nature Portfolio, 2021 11:12818, 10 pages.

(Continued)

*Primary Examiner* — Kennedy Schaetzle
(74) *Attorney, Agent, or Firm* — Perkins Coie LLP

(57) ABSTRACT

Methods and computer systems are described that classify a cardiogram as being an atrial fibrillation (AF) or ventricular fibrillation (VF) cardiogram, automatically detect an AF epoch within an AF cardiogram, and automatically detect a VF epoch within a VF cardiogram. A classification and identification (C&I) system includes a classification system, an AF identification system, and a VF identification system. The C&I system processes cardiograms collected from patients to classify the cardiograms as being AF cardiograms or VF cardiograms and to identify AF epochs within the AF cardiograms or VF epochs within the VF cardiograms. The C&I system may then identify an AF source location of an AF based on the AF epochs and a VF source location of a VF based on the VF epochs. The C&I system may display a graphic of a heart that includes an indication of a source location.

28 Claims, 7 Drawing Sheets

Related U.S. Application Data

(60) Provisional application No. 63/401,106, filed on Aug. 25, 2022.

(51) Int. Cl.
  *A61B 5/355* (2021.01)
  *A61B 5/36* (2021.01)
  *A61B 5/367* (2021.01)
  *G16H 50/20* (2018.01)
  *A61B 18/18* (2006.01)

(52) U.S. Cl.
  CPC ........... *A61B 5/7264* (2013.01); *G16H 50/20* (2018.01); *A61B 5/7267* (2013.01); *A61B 18/18* (2013.01)

(56) References Cited

U.S. PATENT DOCUMENTS

| | | | |
|---|---|---|---|
| 2019/0090769 A1* | 3/2019 | Boleyn | A61B 5/361 |
| 2020/0352462 A1* | 11/2020 | Pedalty | A61B 5/363 |
| 2021/0121090 A1 | 4/2021 | Weinstein et al. | |
| 2021/0401349 A1 | 12/2021 | Schram | |
| 2022/0040473 A1 | 2/2022 | Simon et al. | |
| 2022/0133207 A1 | 5/2022 | Villongco | |
| 2022/0189636 A1* | 6/2022 | Wagner | G06N 3/08 |
| 2022/0346856 A1* | 11/2022 | Fedorov | A61B 34/10 |
| 2023/0335289 A1* | 10/2023 | Kuck | G16H 50/20 |

OTHER PUBLICATIONS

Baumert, M., et al., "Conventional QT Variability Measurement vs. Template Matching Techniques: Comparison of Performance Using Simulated and Real ECG," PLos One, Jul. 2012, vol. 7, issue 7, pp. 1-8.

Krishnamurthy, P., et al., "Comparison of Various Filtering Techniques Used for Removing High Frequency Noise in ECG Signal," International Journal of Students Research in Technology & Management, Jan. 2015, vol. 3 (01), pp. 211-215.

Li, J., et al., "Deep Convolutional Neural Network Based ECG Classification System Using Information Fusion and One-Hot Encoding Techniques," Hindawi, Mathematical Problems in Engineering, vol. 2018, Article ID 7354081, 10 pages.

Vaid, A., "A foundational vision transformer improves diagnostic performance for electrocardiograms," NPJ, Digital Medicine, Seoul National University Bundang Hospital, 2023, 108, 8 pages.

International Search Report and Written Opinion received in Application No. PCT/US23/72854, dated Dec. 29, 2023, 15 pages.

\* cited by examiner

AUTOMATIC FIBRILLATION CLASSIFICATION AND IDENTIFICATION OF FIBRILLATION EPOCHS

CROSS-REFERENCE TO RELATED APPLICATION(S)

This application is a continuation of the International App. No. PCT/US23/72854, filed on Aug. 24, 2023, entitled "Automatic Fibrillation Classification and Identification of Fibrillation Epochs," which claims the benefit of U.S. Pro. App. No. 63/401,106 filed on Aug. 25, 2022, entitled "Automatic Fibrillation Classification and Identification of Fibrillation Epochs," the entire disclosure of each of these applications is incorporated herein by reference.

BACKGROUND

Many heart disorders, such as arrhythmias, can cause symptoms, morbidity (e.g., syncope or stroke), and mortality. Two common types of arrhythmias are atrial fibrillation (AF) and ventricular fibrillation (VF). Both AF and VF are typically caused by cardiac cells that are in some way malfunctioning and sending out signals that produce an irregular heartbeat. Although AF is not typically life-threatening, it can, if not treated, lead to blood clots, strokes, heart failure, and so on. VF, in contrast, is typically life-threatening, and emergency procedures such as a defibrillation shock are typically needed to save the person's life.

A common treatment for both AF and VF is a cardiac ablation. A cardiac ablation attempts to destroy the malfunctioning cells that cause the fibrillation. Several different techniques have been used for performing a cardiac ablation. One technique inserts a catheter into the heart of a patient, moves the catheter to the location of the malfunctioning cells, and destroys the malfunctioning cells by, for example, directing a radiofrequency signal or pulsed electrical field to or freezing the malfunctioning cells. Another technique uses a Stereotactic Ablative Radiotherapy (SABR) device, which noninvasively directs radiofrequency signals to the location of the malfunctioning cells.

Such treatments are typically effective at destroying the malfunctioning cells. However, the treatments are effective only if directed at the location of the malfunctioning cells, which is referred to as the "source location" of the arrhythmia. It has traditionally been difficult to identify the source location with a high degree of certainty. However, advanced technologies have recently become available to assist in the identification of source locations. For example, such advanced technologies are described in U.S. Pat. No. 10,860,754, entitled "Calibration of Simulated Cardiograms" and issued on Dec. 8, 2020, and in U.S. Pat. No. 10,319,144, entitled "Computational Localization of Fibrillation Sources" and issued on Jun. 11, 2019, both of which are hereby incorporated by reference.

DETAILED DESCRIPTION

Figure 1:
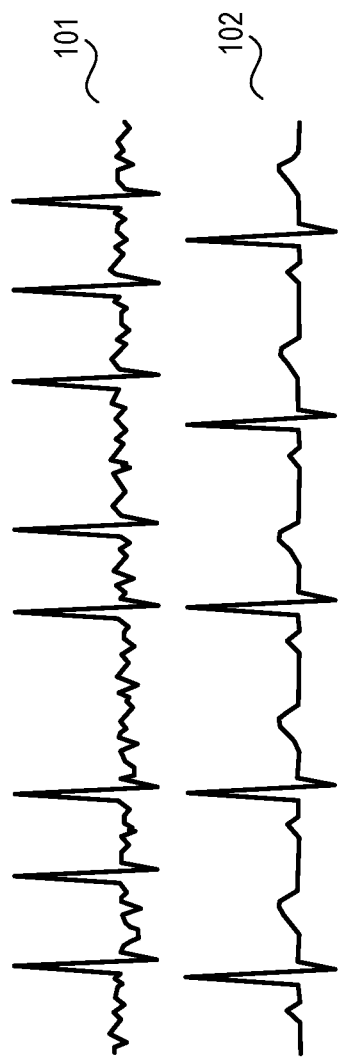
FIG. 1 illustrates an AF ECG and an NSR ECG.

Methods and computing systems are described that classify cardiograms, detect an AF epoch within an AF cardiogram (i.e., collected during an AF episode), and detect a VF epoch within a VF cardiogram (i.e., collected during a VF episode). A classification and identification (C&I) system includes a classification system, an AF identification system, and a VF identification system. An AF epoch is a portion of cardiogram that represents AF, such as an R-R interval during an AF episode. A VF epoch is a portion of a cardiogram that represents VF, such as from the end of pacing to induce VF to the beginning of a defibrillation spike to terminate VF. The C&I system processes cardiograms collected from patients to classify each cardiogram as being an AF cardiogram or a VF cardiogram and to identify AF epochs within the AF cardiograms and VF epochs within the VF cardiograms. The C&I system may then identify one or more AF source locations of an AF based on the AF epochs and one or more VF source locations of a VF based on the VF epochs. The C&I system may identify a source location based on an entire epoch, based on individual cycles, and/or based on multiple cycles. A cardiogram can be an electrocardiogram (ECG), a vectorcardiogram (VCG), or other or other electrogram that is a measurement of the electrical activity of a heart. This Detailed Description primarily describes a C&I system that is adapted to process ECGs because an ECG is the most common type of cardiogram. The C&I system could also be adapted to process other types of cardiograms. Given an input cardiogram, the C&I system may convert the input cardiogram to a cardiogram of the type to which it is adapted to process. For example, if adapted to process a VCG, the C&I system can convert an input ECG to a VCG for processing.

An ECG may be considered to represent an AF ECG if it has an AF epoch, for example, within a T-Q interval, an S-Q interval, and a R-R interval, and to represent a VF ECG if it has a VF epoch, for example, within a T-Q interval or an interval from the end of pacing pulses to the start of a defibrillation spike. The C&I system may process an ECG to identify various ECG landmarks, such as P, Q, R, S, and T peaks. The term "peak" refers to a local maximum (i.e., positive peak) or a local minimum (i.e., negative peak) of an ECG. From the ECG landmarks, the C&I system identifies ECG regions such as QRS complexes, T waves, P waves, Q-T intervals, T-Q intervals, T-P intervals, R-R intervals, and so on. To identify ECG landmarks and ECG regions, the C&I system may employ a Pan-Tompkins algorithm or other algorithms such as those available via open-source software systems. One open-source software algorithm is published in GitHub as described in Makowski, D., Pham, T., Lau, Z. J., Brammer, J. C., Lespinasse, F., Pham, H., Schölzel, C., & Chen, S. A., NeuroKit2: A Python toolbox for neurophysiological signal processing, *Behavior Research Methods*, 53(4), pp. 1689-1696 (2021). As an initial step (e.g., before identifying landmarks), the C&I system may remove noise from the ECG using a noise-reduction algorithm such as the algorithm described in Krishnamurthy, P., Swethaanjali, N. and Lakshmi, A. B., "Comparison of Various Filtering Techniques Used for Removing High Frequency Noise in ECG Signal," Int'l Journal of Students' Research in Technology & Management, 3(1), pp. 211-215 (2015), which is hereby incorporated by reference. An ECG that is to be processed may be encoded based on an ECG file format such as an Annotated ECG Waveform Data Standard (aECG) format, an Extensible Markup Language (XML) format, a Digital Imaging and Communications in Medicine (DICOM) format, a Joint Photographic Experts Group (JPEG) format, and so on.

Classification System

The classification system processes an ECG to classify it as an AF ECG, a VF ECG, or neither. If an ECG represents neither an AF ECG nor a VF ECG, it may represent, for example, a normal sinus rhythm (NSR) ECG or an atrial flutter ECG. The classification system may employ one or more classification machine learning (ML) models that input a feature vector that includes ECG features derived from an ECG and that output a classification of the ECG. The ECG features may include, for example, an ECG (e.g., an image or a voltage-time series), a portion of an ECG, a QRS integral, and/or other features derived from the ECG (e.g., landmarks). In some embodiments, the classification system employs a classification ML model for each arrhythmia type that inputs ECG features and outputs a classification such as AF ECG, VF ECG, or neither. For example, an AF classification ML model may be employed to determine whether ECG data represents an AF ECG, and a VF classification ML model may be employed to determine whether ECG data represents a VF ECG. The classification system may alternatively employ a classification ML model that inputs ECG features and outputs a classification indicating which of one or more arrythmia types (e.g., AF and VF), if any, that the ECG represents.

A classification ML model may be trained based on a collection of ECGs along with a classification of whether each ECG represents a fibrillation arrythmia type (AF or VF) or not. For each ECG, the classification system generates a feature vector based on that ECG and labels the feature vector based on the classification. The classification system then trains a classification ML model using training data that includes the feature vectors and their labels. The collection of ECGs may include clinical ECGs that are collected from patients and/or simulated ECGs along with their classifications. The classification for a clinical ECG may be specified by a specialist, and a classification for a simulated ECG may be specified based on the simulation data. The classification system labels a feature vector derived from a training ECG with its classification.

The simulated ECGs may be generated by simulating electrical activity of a heart with various characteristics such as size, orientation, action potential, conduction velocity, scar tissue, source location of an arrhythmia, arrhythmia type (e.g., AF or VF) (if any), location of a prior ablation, and so on. The simulated ECGs may be generated as described in U.S. Pat. Nos. 10,860,754 and 10,319,144. A simulated ECG may be generated based on the output of each simulation of electrical activity.

The classification system may derive features of an ECG by first identifying ECG landmarks and at least one ECG region, such as the T-Q interval, R-Q interval, or R-R interval within the ECG. The classification system then may extract from an ECG region a segment of a fixed size (e.g., 100 ms) from the start or end of the ECG region or segments of various sizes (e.g., 50 ms, 100 ms, and 200 ms). Instead of each segment including the start or end of the ECG region, a sliding window (e.g., increments of 10 ms) may be used so that segments start and end at various offsets within the ECG region. The features may be size and offset of a window, average voltage in a window, number of nonstandard peaks in a window, and so on. The classification system may employ other features alone or in combination with those described above, such as a feature that is an image of the ECG, a feature that is a time series of voltages, and so on. The C&I system may select features for training that are deemed relevant by employing various feature selection techniques. (See Johnson, K., and Kuhn, M., "Applied Predictive Modeling," Springer, 2013, which is hereby incorporated by reference.) The output of an ML model may be a probability that the input features represent a classification, such as 0.90 for the AF classification, 0.03 for the VF classification, and 0.07 for neither classification. The classification system may employ an ensemble of classification ML models, such as one for each length of a window or for each different sets of features. One set of features may include average voltage and number of nonstandard peaks, and another set of features may include an image of an ECG. The classifications of the ensemble can be combined to generate an overall classification for the ECG.

The classification system may employ one or more supervised and/or unsupervised ML models for the classification ML model. A supervised classification ML model may be a neural network, a recurrent neural network (RNN), a convolutional neural network (CNN), or a support vector machine (SVM). An unsupervised classification ML model may be a k-means clustering model. Other supervised and unsupervised ML models may be employed such as those described below. The classification system may also employ an ensemble of ML models that, for example, includes an RNN, a k-means clustering model, and an SVM. The RNN may inputs a voltage-time series and outputs an initial classification, and the k-means clustering model inputs features derived from the voltage-time series and outputs an initial classification. The SVM inputs both initial classifications and outputs a final classification. As another example, an ensemble of ML models may include a CNN autoencoder that inputs an ECG image and outputs a latent vector and another ML model (e.g., SVM or a neural network (NN)) that inputs the latent vector and outputs the classification. The classification system may employ classification ML models that may be considered classifiers or regressors. A regressor generates a continuous value from a continuous domain (e.g., real numbers), and a classifier generates a discrete value from a discrete domain (e.g., classes). Although a classifier generates a discrete value indicating a class, it may also generate a continuous value for each class representing a probability. The continuous values generated by a regressor may be mapped to classes.

In some embodiments, the classification system may employ a generative adversarial network (GAN) as described below. A GAN may be used to train a discriminator for classifying an ECG as or not an AF may be trained using images of AF ECGs such as R-R intervals. A discriminator may also be trained to classify other types of arrhythmias.

In some embodiments, the classification system may employ an attention mechanism (e.g., an encoder of a transformer) to generate an encoding. The attention mechanism may be trained in parallel with an ML model to classify ECGs, for example, as AF or VF. The input to the attention mechanism may be tokens that represent portions of an ECG, such as cycles within a R-R interval, time ranges within a R-R interval, and so on. The portions may be represented as images, time-voltage series, or features derived from the ECG (e.g., average voltage or QRS integral). The output of the attention mechanism is a latent vector that is an optimized representation of the ECG for classification by the ML model. The ML model may be, for example, an NN or an SVM.

In some embodiments, the classification system may employ an NN or a CNN to classify ECGs as AF or VF. When an NN is employed, the training data may include feature vectors with features derived from ECG images or ECG time-voltage series that are labeled as AF, VF, or neither. When a CNN is employed, the training data may include feature vectors with a feature that is an ECG image along with their labels. A separate ML model may be trained to classify AF ECGs and VF ECGs.

In some embodiments, the classification system may employ k-means clustering to classify ECGs as AF or VF. When k-means clustering is employed, the inputs may be ECG images or ECG time-voltage series of AF, VF, NSR, and other arrhythmias. The k-means clustering generates clusters of similar ECGs with one or more clusters representing each of AF, VF, or neither. The clusters that represent AF and VF are then identified and labeled as being AF, VF, or neither (e.g., by a person). To determine the classification for a patient ECG, the cluster with ECGs that are most similar to the patient ECG is identified, and the patient ECG is classified according to the cluster's label. Various similarity metrics may be employed, such as cross-correlation based on a mean or median ECG of a cluster. In some embodiments, a supervised ML model may be trained using the ECG of the clusters labeled with the labels of the clusters.

AF Identification System

An AF is characterized by irregular cardiac cycles (e.g., different lengths of the R-R intervals) and a rapid heart rate (e.g., 120 bpm). FIG. 1 illustrates an AF ECG and an NSR ECG. The upper ECG 101 is an AF ECG, and the lower ECG 102 is an NSR ECG. The AF ECG has R-R intervals of different lengths, such as 400 ms and 800 ms, and represents a heart rate of approximately 175 bpm. The AF ECG has no discernable T waves or P waves, and the T-Q intervals (AF epochs) have irregular waves with irregular shapes (e.g., height and width) and irregular spacing. In contrast, the NSR ECG has R-R intervals of approximately the same length, that is, 800 ms, and represents a heart rate of approximately 75 bpm. The NSR ECG has distinct T waves and P waves.

To identify the AF epochs, the AF identification system may identify the T-Q intervals and then identify which T-Q intervals contain AF epochs. The T-Q intervals may have been previously identified if the classification system is employed to identify AF ECGs, may be identified using various techniques such as those used by the classification system for identifying T-Q intervals, or may be pre-classified. Various ML models may also be employed to identify T-Q intervals, such as a CNN trained on ECG images labeled with their T-Q intervals or an NN (or SVM) trained on ECG voltage-time series. If there is no discernable T wave in an R-R interval, for purposes of AF identification, the T-Q interval may be defined as having a T wave that is a certain offset from the first R peak of the R-R interval (e.g., 250 ms) with the T-Q interval ending at the onset of the next R peak.

Such an R-R interval may be required to satisfies a minimum length criterion (e.g., >750 ms). If the criterion is not satisfied, that R-R interval is not used to identify an AF epoch. Alternatively, a T-Q interval of an R-R interval with no discernable T wave may be defined as having a T wave and an ending based on percentages of the distance from the first R peak to second R peak of the R-R interval. For example, the T wave may be considered be at 30% of the distance, and the ending may be at 90% of the distance.

The AF identification system then identifies which T-Q intervals represent AF epochs. The AF identification system may employ an AF epoch ML model to identify the AF epochs. The AF epoch ML model may be a supervised and/or an unsupervised ML model, such as one of the ML models described above or an ensemble of those ML models, which identifies AF epochs. The AF identification system may generate the training data from a collection of training AF ECGs with T-Q intervals marked as representing AF epochs or non-AF epochs. The training AF ECGs may include simulated AF ECGs and/or clinical AF ECGs. The AF identification system may augment the training AF ECGs by generating augmented AF ECGs for each patient AF ECG. The AF identification system may generate an augmented AF ECG by adding simulated noise to a patient AF ECG, time-shifting the patient AF ECG (e.g., moving the T wave to start at a later time), stretching (or compressing) the patient AF ECG (e.g., stretching a cardiac cycle from 0.4 seconds to 0.5 seconds), and so on. The simulated AF ECGs may be generated as described above.

The AF identification system identifies T-Q intervals (e.g., as described above) of the training data and may extract features from the T-Q intervals, such as an image of a T-Q interval, a voltage-time series of a T-Q interval, the number of AF cycles within a T-Q interval, the area under the curve after inverting negative peaks within a T-Q interval, or other features relating to a T-Q interval as described above.

The AF identification system may employ any of the ML models described above for the classification system. When the AF epoch ML model is a supervised ML model, the AF identification system labels feature vectors with features derived from the T-Q intervals of the training data as being AF epochs or non-AF epochs as specified by the training data. The AF identification system then trains the supervised ML model using the labeled feature vectors. To identify the AF epochs in a patient ECG, the AF identification system identifies a T-Q interval and extracts features and then inputs a feature vector with those features into that supervised ML model, which outputs a classification indicating whether that T-Q interval is an AF epoch or a non-AF epoch.

When the AF epoch ML model is unsupervised, the AF identification system may employ a k-means clustering model to generate clusters of the T-Q intervals. If two clusters are used, then one cluster would represent AF epochs and the other cluster would represent non-AF epochs. If more than two clusters are used, then multiple clusters may represent T-Q intervals of different lengths or AF epochs with different characteristics (e.g., different numbers or shapes of AF cycles). After clustering, the clusters that represent AF epochs may be manually identified and labeled. To identify the AF epochs in an ECG, the AF identification system identifies the T-Q intervals, generates a patient feature vector of features extracted from the ECG, and then identifies the cluster whose feature vectors are most similar to the patient feature vector, using a similarity metric as described above. The label associated with the identified cluster is the label for the T-Q interval.

In some embodiments, the AF identification system may perform the training on a single lead, such as lead II. Alternatively, the AF identification system may perform the training based on multiple leads, for example, by generating an ML model for each lead. To identify the AF epoch, the AF identification system may identify a T-Q interval as an AF epoch based on it being classified as an AF epoch on a certain number of the leads (e.g., 9 out of 12 leads). The AF identification system may also weight the leads differently, such as giving lead II more weight than lead aVL. In such a case, the AF identification system may generate an AF epoch score, for example, as the sum of the probability of each lead that is output by the ML model for that lead times the weight of that lead. If the AF epoch score satisfies an AF epoch score criterion (e.g., greater than a threshold percentage of the maximum possible AF epoch score), the T-Q interval is considered to represent an AF epoch. The AF epoch score criterion may be established based on desired accuracy of the classifications. The AF epoch score criterion may also be derived from AF epochs of the training data or a hold-out portion of the training data, for example, by ensuring that the vast majority of those AF epochs will satisfy the AF epoch score criterion. The weights of the leads may be based on how well each lead distinguishes AF epochs from non-AF epochs. The weights may be established based on analysis of the accuracy of the ML model in classifying the training T-Q intervals. For example, a gradient descent optimization technique may be employed to find weights that tend to minimize an objective function such as one based on the number of correct and incorrect classifications, which may be biased to allow for incorrect classifications of some AF epochs to help ensure that no non-AF epochs are incorrectly classified. The output of each ML model for a lead may also be input to an aggregation ML model (e.g., support vector machine) which outputs the classification. The ML models for the leads and the aggregation ML model may be trained separately or in parallel.

The AF identification system may employ a mapping system to identify a source location associated with an AF epoch. The AF identification system may employ a mapping system as described in the '754 and '144 patents. The mapping system may be developed based on simulated AF epochs and/or clinical AF epochs. The simulated AF epochs may be generated by running simulations of electrical activity of hearts with various characteristics, such as a source location of an AF. Each simulation is run until the simulation stabilizes or until a termination simulation time (e.g., 10 seconds of simulated electrical activity) is reached. A simulation stabilizes when the cardiac cycles satisfy a stabilization criterion such as the cardiac cycles being similar to each other, for example, because they represent an AF episode. Techniques for determining stability are described in Krummen, D., et al., Rotor Stability Separates Sustained Ventricular Fibrillation from Self-Terminating Episodes in Humans, Journal of the American College of Cardiology, Vol. 63, No. 24, 2014, which is hereby incorporated by reference. A T-Q interval or portion of a T-Q interval within one of the stable cardiac cycles is a simulated AF epoch. The source location used in the simulation is associated with the simulated AF epoch. Each clinical AF epoch may be associated with a source location that may correspond to the location of an ablation that was successful in treating the AF. The AF identification system may generate a library of mappings of AF epochs to their associated source locations. An AF epoch mapping ML model may be generated based on feature vectors with features derived from an AF epoch labeled with its source location. (See, e.g., U.S. Pat. No. 10,860,754.)

The AF identification system may identify AF cycles of an AF epoch from an AF VCG corresponding to an AF ECG using various techniques. For example, one technique employs the axis with the greatest amplitude as a reference axis. The technique then identifies where an AF VCG tracing for an AF epoch crosses the reference axis in a certain direction (e.g., from negative to positive) and designates that crossing as a start of an AF cycle. The technique then identifies when the AF VCG tracing next crosses the reference axis in the certain direction. The technique may employ a blanking window (e.g., 50 ms) after the start of an AF epoch during which crossings are ignored to account for jitter in the VCG tracing, which may cause multiple crossings in a very short period. The crossing delimits the start of an AF cycle (except for the last crossing) and the end of the prior AF cycle (except for the first crossing). Another technique identifies a reference axis using principal component analysis (PCA). Such a reference axis will help ensure the spatial direction for tracking crossings contain the maximum variation in voltage.

When generating the training data, the AF identification system may filter out AF cycles that do not meet an AF cycle criterion. The AF cycle criterion may be based on an area under the curve that is less than a certain percent larger (e.g., 25% larger) than the average of the AF cycles of the AF epoch and/or an AF cycle length that is less than a certain percent longer (e.g., 50% longer) than the average of the AF cycles of the AF epoch. The AF identification system may also filter out AF epochs that are determined (e.g., by a person) to be false positives.

The AF identification system may also employ an AF cycle ML model to identify AF cycles directly from a VCG. The training data may be based on clinical and/or simulated data. The clinical data and the simulated data may have AF cycles manually demarcated or demarcated using the techniques described above to identify AF cycles. The AF cycle ML model may be based on a recurrent neural network that inputs a voltage-time series of an ECG and outputs an indication of the cycles. The AF cycle ML model may also be an NN or a CNN that inputs portions of an ECG (e.g., with varying window sizes) and outputs an indication of the portions that represent an AF cycle. The AF cycle ML model may also employ an attention mechanism as described above.

To identify a potential source location of an AF for a patient given a patient AF ECG, the AF identification system may first identify patient T-Q intervals that are patient AF epochs using the AF epoch ML model. The AF identification system then identifies the patient AF cycles of the patient AF epochs and may filter out the patient AF cycles that do not meet the AF cycle criterion. The AF identification system then employs the mapping system as described above to identify the source location associated with one or more patient AF cycles.

The AF identification system then outputs indications of the source locations (e.g., identified by a mapping system as described above). The AF identification system may display a graphic of a heart with the source locations identified. The graphic may use various intensities of colors for a source location to illustrate the number of cycles that have that source location or very similar source locations, referred to as a cluster of source locations. A cluster representing a majority of the AF cycles may represent an actual source location of the AF for the patient. The display of a graphic of a heart with source locations is described in U.S. Pat. App.

Pub. No. 2022-0133207 entitled "Heart Graphic Display System" and published on May 5, 2022, which is hereby incorporated by reference.

The AF identification system may also display an ablation pattern on the graphic of the heart to help inform a treatment decision on an ablation pattern to use in treating the AF. The ablation pattern may be a common ablation pattern associated with one or more of the source locations. A wide area circumferential ablation (WACA) line and a left anterior (LA) roof line are examples of common ablation patterns. The AF identification system may also identify an ablation pattern based on simulations of electrical activity of a heart or clinical data indicating what ablation patterns would be effective in treating an AF associated with one or more of the source locations. Techniques for identifying such simulated ablation patterns are described in U.S. Pat. No. 11,259,871 entitled "Identify Ablation Pattern for Use in an Ablation" and granted on Mar. 1, 2022, which is hereby incorporated by reference. The clinical data may be mappings of one or more source locations to an ablation pattern that was successful in treating an AF associated with those one or more source locations. The mappings may be derived from electronic medical records (EMR) of a collection of patients. Such patients may be selected based on having similar characteristics to the patient being treated.

The AF identification system may also demarcate a source location onto a computed tomography (CT) scan of the patient. The CT scan can then be input to an ablation therapy device, such as a SABR device. The ablation therapy device can be used to plan and perform the ablation at the source location. The AF identification system may be used in conjunction with the overall ablation workflow system as described in PCT App. No. US23/14406, entitled "Overall Ablation Workflow System" and filed on Mar. 2, 2023, which is hereby incorporated by reference.

Vf Identification System

To induce a VF in a subject, the subject's heart is first paced near the source location of the VF at a pacing interval (e.g., 0.01 seconds). The pacing is stopped when the VF is induced. The VF is then terminated by a defibrillation shock.

Figure 2:
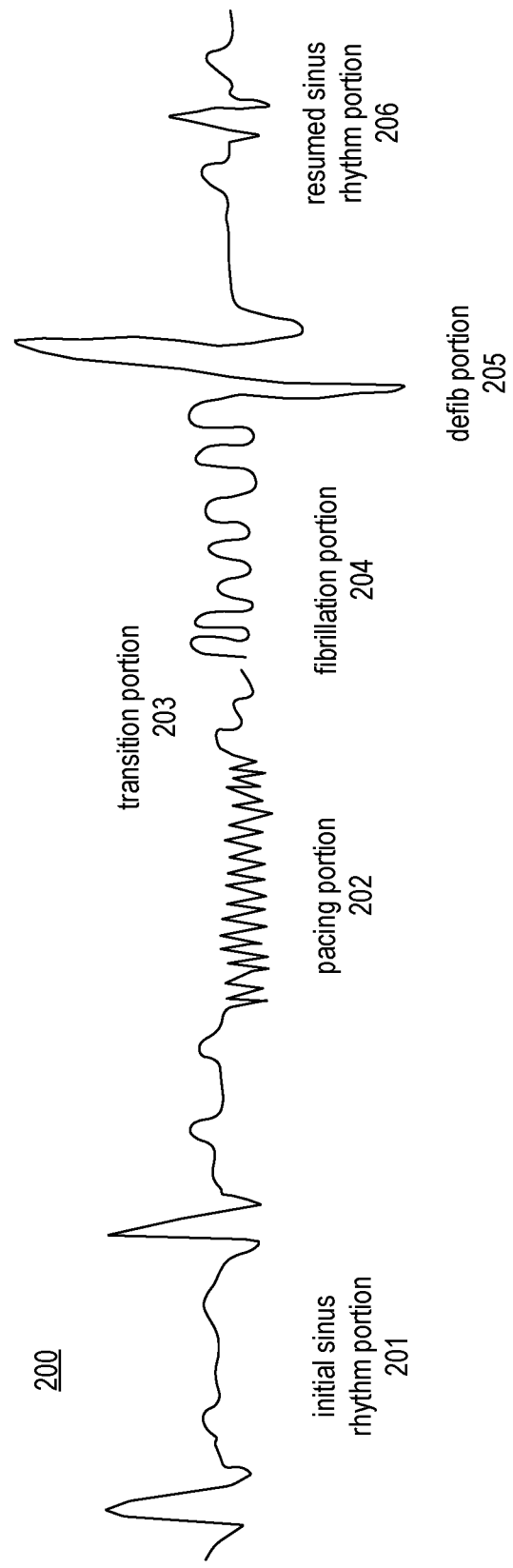
FIG. 2 illustrates an example of a VF ECG collected during an induced VF.

FIG. 2 illustrates an example of a VF ECG collected during an induced VF. The VF ECG 200 includes an initial NSR portion 201, a pacing portion 202, a transition portion 203, a VF portion 204, a defibrillation portion 205, and a resumed NSR portion 206. The initial NSR portion represents NSR prior to the start of pacing. The pacing portion includes a sequence of pacing cycles, each with a pacing spike that results from the application of a pacing pulse. The frequency of the pacing cycles is typically very high relative to the frequency of the VF cycles within a VF epoch. The VF portion (also referred to as a VF epoch) starts when a VF is induced and ends when a defibrillation shock is applied. The VF epoch includes VF cycles that are each delimited by adjacent crossing of a baseline voltage (e.g., an average voltage or zero voltage) in the same direction. The defibrillation portion represents the application of the defibrillation shock. The resumed NSR portion represents NSR after the VF defibrillation shock is applied. Some VF ECGs may not include the initial NSR portion and/or the resumed NSR portion. If a VF ECG represents a VF that is not induced (e.g., collected in an emergency situation), then the VF ECG would not include a pacing portion.

A VF identification system detects a VF epoch in a VF ECG that is collected, for example, during a procedure to induce a VF. The VF identification system may first identify the start of the defibrillation portion, which is at the end of the VF portion, and then identify the end of the pacing portion by processing the ECG in reverse time order. Alternatively, the VF identification system may first identify the pacing portion and then identify the defibrillation portion by processing the ECG in time order. The VF identification system may preprocess the ECG by initially applying a band-pass filter to filter out low frequencies.

The VF identification system may apply various techniques to detect the defibrillation spike, such as applying a match filter, detecting the presence of a large negative voltage followed by a large positive voltage, applying an ML model to distinguish between defibrillation spikes and non-defibrillation spikes, and so on. A supervised ML model may be trained using VF spikes labeled as VF spikes and other portions of an ECG labeled as non-VF spikes. The VF identification system may employ various ML models such as an RNN, a CNN, or a transformer. An unsupervised ML model (e.g., k-means clustering) may be trained using VF spikes and other portions of an ECG. To identify a defibrillation spike, the VF identification system may start at either end of the ECG and, using a sliding window of various sizes at various offsets, determine whether each window includes a defibrillation spike.

Once a defibrillation spike is detected, the VF identification system may assume that the VF epoch ends just before the defibrillation spike. To locate the beginning of the VF epoch, the VF identification system may process the VF ECG in the reverse time order starting with the defibrillation spike. The VF identification system may also preprocess the ECG by taking the square root of the square of the voltages to convert the negative voltages into positive voltages. As a result, the VF epoch and the pacing portion will have twice as many positive peaks and no negative peaks.

The VF identification system may apply a combination of techniques to identify the start of a VF epoch, such as the detection of cycles that may represent a pacing cycle or a VF cycle. A combined technique may generate a VF cycle score, such as the probability of being a VF cycle, and a pacing cycle score, such as the probability of being a pacing cycle. A high VF cycle score and a low pacing cycle score indicate a VF cycle, a low VF cycle score and a high pacing cycle score indicate a pacing cycle, and a low VF cycle score and a low pacing cycle score indicate a transition portion. The VF cycle score and the pacing cycle score may be generated using an ML model that is trained using training data that includes a feature vector for each training pacing cycle labeled as a pacing cycle and each training VF cycle labeled as a VF cycle. Features of the feature vectors may include various characteristics of a cycle such as a voltage-time series, an image of the cycle, the maximum amplitude of the cycle, and so on. The ML model may output a probability that the input cycle represents a pacing cycle and a probability that the input cycle represents a VF cycle. The ML model may be, for example, an RNN, a CNN, an SVM, an NN, or a transformer.

The VF identification system may identify a pacing portion and a VF epoch based on the frequency and/or shape of cycles. The frequency of the peaks in a VF epoch is typically much lower and less regular than the frequency of the pacing cycles. To identify based on frequency, the VF identification system may assign a frequency to each cycle based on the frequency of the cycles within a time window centered at that cycle. When the frequency generated for a cycle changes, for example, by a threshold percentage (or satisfies another frequency change criterion) from the frequency of a cycle that is just outside of the defibrillation spike side of the window, the VF identification system may assume that the cycle that is just outside is the start of the VF epoch. The frequency may be calculated based on a Fast Fourier Transform (FFT), a count of peaks, a frequency histogram, and so on.

The shape of a VF cycle is typically less steep and wider than the shape of a pacing cycle. To identify based on shape, the VF identification system may input a signature (i.e., shape) of a pacing cycle and apply a match filter to cycles to differentiate pacing cycles from non-pacing cycles. In such a case, the VF identification system may process an ECG before a defibrillation spike to identify the last pacing cycle. The VF cycle may be considered to begin after a time interval that is based on a typical length of a transition portion. The signature of a pacing spike may be input to the VF identification system or derived from known pacing portions of VF ECGs.

Another technique to identify the start of a VF epoch is based on similarity of VF cycles. When a VF is induced, it may take some time for the VF to stabilize. The VF cycles towards the end of a VF epoch (just before the defibrillation spike) are likely VF cycles after the VF has stabilized. The cycles that are similar to those VF cycles are likely VF cycles. The VF identification system may designate a template VF cycle that may be one of the VF cycles near the end of the VF epoch or a combination (e.g., average) of those VF cycles. The VF identification system generates similarity scores between the template cycle and cycles prior to the template VF cycle. The start of the VF epoch may be considered to be the earliest cycle, in a sequence of cycles ending with the template VF cycle, whose similarity to the template VF cycle satisfies a similarity criterion. The sequence of the similar cycles represents the VF cycles of the VF epoch. The VF identification system may employ various techniques for generating the similarity scores, such as a Pearson correlation, a Spearman's rank correlation, a cosine similarity, and so on. The similarity criterion may be based on a similarity threshold determined based on analysis of sample VF ECGs with VF cycles labeled. The similarity threshold may be the average of the average similarity scores of each VF cycle.

To identify a potential source location of a VF for a patient given a patient VF ECG, the VF identification system may first identify patient VF epochs as described above. The VF identification system then employs the mapping system (described above) to identify the source location associated with one or more patient VF cycles. The VF identification system then outputs indications of the source locations. The VF identification system may display a graphic of a heart with the source locations identified as described above for the AF identification system. The VF identification system may also demarcate a source location onto a CT scan of the patient and input it to an ablation therapy device as described above for the AF identification system.

In some embodiments, the VF identification system may employ a VF epoch ML model to identify VF epochs. The VF epoch ML model may be trained using training data that include features derived from VF ECGs (i.e., simulated or clinical) and, if supervised, labels indicating VF epochs. Any of the ML models described above for the classification system may be employed for the VF epoch ML model.

The VF identification system may also employ a defibrillation spike ML model to identify defibrillation spikes. The defibrillation spike ML model may be trained using cardiograms labeled with portions that contain a defibrillation spike or that contain no defibrillation spike. The training may be based on features derived from the portions, such as maximum voltage, area under the curve, width (time), and so on. The defibrillation spike ML model may include an SVM, a GAN, an NN, a CNN, an RNN, a transformer, and so on. After the defibrillation spike model is trained, the VF identification system uses it to identify defibrillation spikes in a VF ECG.

The computing systems (e.g., network nodes or collections of network nodes) on which the C&I system and the other described systems may be implemented may include a central processing unit, input devices, output devices (e.g., display devices and speakers), storage devices (e.g., memory and disk drives), network interfaces, graphics processing units, communications links (e.g., Ethernet, Wi-Fi, cellular, and Bluetooth), global positioning system devices, and so on. The input devices may include keyboards, pointing devices, touch screens, gesture recognition devices (e.g., for air gestures), head and eye tracking devices, microphones for voice recognition, and so on. The computing systems may include high-performance computing systems, distributed systems, cloud-based computing systems, client computing systems that interact with cloud-based computing systems, desktop computers, laptops, tablets, e-readers, personal digital assistants, smartphones, gaming devices, servers, and so on. The computing systems may access computer-readable media that include computer-readable storage mediums and data transmission mediums. The computer-readable storage mediums are tangible storage means that do not include a transitory, propagating signal. Examples of computer-readable storage mediums include memory such as primary memory, cache memory, and secondary memory (e.g., DVD), and other storage. The computer-readable storage media may have recorded on them or may be encoded with computer-executable instructions or logic that implements the C&I system and the other described systems. The data transmission media are used for transmitting data via transitory, propagating signals or carrier waves (e.g., electromagnetism) via a wired or wireless connection. The computing systems may include a secure crypto processor as part of a central processing unit (e.g., Intel Secure Guard Extensions (SGX)) for generating and securely storing keys, for encrypting and decrypting data using the keys, and for securely executing all or some of the computer-executable instructions of the C&I system. Some of the data sent by and received by the C&I system may be encrypted, for example, to preserve patient privacy (e.g., to comply with government regulations such as the European General Data Protection Regulation (GDPR) or the Health Insurance Portability and Accountability Act (HIPAA) of the United States). The C&I system may employ asymmetric encryption (e.g., using private and public keys of the Rivest-Shamir-Adleman (RSA) standard) or symmetric encryption (e.g., using a symmetric key of the Advanced Encryption Standard (AES)).

The one or more computing systems may include client-side computing systems and cloud-based computing systems (e.g., public or private) that each execute computer-executable instructions of the C&I system. A client-side computing system may send data to and receive data from one or more servers of the cloud-based computing systems of one or more cloud data centers. For example, a client-side computing system may send a request to a cloud-based computing system to perform tasks such as running a patient-specific simulation of electrical activity of a heart or training a patient-specific ML model. A cloud-based computing system may respond to the request by sending to the client-side computing system data derived from performing the task, such as a source location of an arrhythmia. The servers may perform computationally expensive tasks in advance of processing by a client-side computing system, such as training an ML model, or in response to data received from a client-side computing system. A client-side computing system may provide a user experience (e.g., user interface) to a user of the C&I system. The user experience may originate from a client-side computing device or a server computing device. For example, a client-side computing device may generate a patient-specific graphic of a heart and display the graphic. Alternatively, a cloud-based computing system may generate the graphic (e.g., in a HyperText Markup Language (HTML) format or an Extensible Markup Language (XML) format) and provide it to the client-side computing system for display. A client-side computing system may also send data to and receive data from various medical devices such as an ECG monitor, an ablation therapy device, an ablation planning device, and so on. The data received from the medical devices may include an ECG, actual ablation characteristics (e.g., ablation location and ablation pattern), and so on. The data sent to a medical device may include, for example, data in a Digital Imaging and Communications in Medicine (DICOM) format. A client-side computing device may also send data to and receive data from medical computing systems that store patient medical history data, descriptions of medical devices (e.g., type, manufacturer, and model number) of a medical facility, results of procedures, and so on. The term "cloud-based computing system" may encompass computing systems of a public cloud data center provided by a cloud provider (e.g., Azure provided by Microsoft Corporation) or computing systems of a private server farm (e.g., operated by the provider of the C&I system).

The C&I system and the other described systems may be described in the general context of computer-executable instructions, such as program modules and components, executed by one or more computers, processors, or other devices. Generally, program modules or components include routines, programs, objects, data structures, and so on that perform tasks or implement data types of the C&I system and the other described systems. Typically, the functionality of the program modules may be combined or distributed as desired in various examples. Aspects of the C&I system and the other described systems may be implemented in hardware using, for example, an application-specific integrated circuit (ASIC) or a field programmable gate array (FPGA).

An ML model employed by the C&I system may be any of a variety or combination of supervised, semi-supervised, self-supervised, or unsupervised ML models including a neural network, such as a fully connected, convolutional, recurrent, or autoencoder neural network, or a restricted Boltzmann machine, a support vector machine, a Bayesian classifier, a k-means clustering model, a decision tree, a generative adversarial network, a transformer, and so on. When the ML model is a deep neural network, the model is trained using training data that includes features derived from data and labels corresponding to the data. For example, the data may be images of ECGs with a feature being the image itself, and the labels may be a characteristic indicated by the ECGs (e.g., normal sinus rhythm). The training results in a set of weights for the activation functions of the layers of the deep neural network. The trained deep neural network can then be applied to new data to generate a label for that new data. When the ML model is a support vector machine, a hyper-surface is found to divide the space of possible inputs. For example, the hyper-surface attempts to split the positive examples (e.g., images of normal sinus rhythm ECGs) from the negative examples (e.g., images of arrhythmia ECGs) by maximizing the distance between the nearest of the positive and negative examples to the hyper-surface. The trained support vector machine can then be applied to new data to generate a classification (e.g., normal sinus rhythm or arrhythmia) for the new data. An ML model may generate values of a discrete domain (e.g., classification), probabilities, and/or values of a continuous domain (e.g., regression value, classification probability).

Various techniques can be used to train a support vector machine, such as adaptive boosting, which is an iterative process that runs multiple tests on a collection of training data. Adaptive boosting transforms a weak learning algorithm (an algorithm that performs at a level only slightly better than chance) into a strong learning algorithm (an algorithm that displays a low error rate). The weak learning algorithm is run on different subsets of the training data. The algorithm concentrates increasingly on those examples in which its predecessors tended to show mistakes. The algorithm corrects the errors made by earlier weak learners. The algorithm is adaptive because it adjusts to the error rates of its predecessors. Adaptive boosting combines rough and moderately inaccurate rules of thumb to create a high-performance algorithm. Adaptive boosting combines the results of each separately run test into a single, very accurate classifier. Adaptive boosting may use weak classifiers that are single-split trees with only two leaf nodes.

A neural network model has three major components: an architecture, a loss function, and a search algorithm. The architecture defines the functional form relating the inputs to the outputs (in terms of network topology, unit connectivity, and activation functions). The search in weight space for a set of weights that minimizes the loss function is the training process. A neural network model may use a radial basis function (RBF) network and a standard or stochastic gradient descent as the search technique with backpropagation.

A convolutional neural network (CNN) has multiple layers such as a convolutional layer, a rectified linear unit (ReLU) layer, a pooling layer, a fully connected (FC) layer, and so on. Some more complex CNNs may have multiple convolutional layers, pooling layers, and FC layers. Each layer includes a neuron for each output of the layer. A neuron inputs outputs of prior layers (or original input) and applies an activation function to the inputs to generate an output.

A convolutional layer may include multiple filters (also referred to as kernels or activation functions). A filter inputs a convolutional window, for example, of an image, applies weights to each pixel of the convolutional window, and outputs a value for that convolutional window. For example, if the static image is 256 by 256 pixels, the convolutional window may be 8 by 8 pixels. The filter may apply a different weight to each of the 64 pixels in a convolutional window to generate the value.

An activation function has a weight for each input and generates an output by combining the inputs based on the weights. The activation function may be a rectified linear unit (ReLU) that sums the values of each input times its weight to generate a weighted value and outputs max(0, weighted value) to ensure that the output is not negative. The weights of the activation functions are learned when training an ML model. The ReLU function of max(0,weighted value) may be represented as a separate ReLU layer with a neuron for each output of the prior layer that inputs that output and applies the ReLU function to generate a corresponding "rectified output."

A pooling layer may be used to reduce the size of the outputs of the prior layer by downsampling the outputs. For example, each neuron of a pooling layer may input 16 outputs of the prior layer and generate one output, resulting in a 16-to-1 reduction in outputs.

An FC layer includes neurons that each input all the outputs of the prior layer and generate a weighted combination of those inputs. For example, if the penultimate layer generates 256 outputs and the FC layer inputs a neuron for each of three classifications (e.g., AF, VF, AFL), each neuron inputs the 256 outputs and applies weights to generate a value for its classification.

An unsupervised ML technique trains an ML model using unlabeled training data. K-means clustering is an example of an ML technique. Given feature vectors representing the training data, k-means clustering clusters the feature vectors into clusters of similar feature vectors. With k-means clustering, the number of clusters may be predefined. For example, the classification system may employ three clusters (k=3) to represent a cluster of AF ECGs, a cluster of VF ECGs, and a cluster of neither. An example training technique initially randomly places a feature vector in each cluster. The training then repeatedly calculates a mean feature vector of each cluster, selects a feature vector not in a cluster, identifies the cluster whose mean is most similar, adds the feature vector to that cluster, and moves the feature vectors already in the clusters to the cluster with the most similar mean. Similarity may be determined, for example, based on a Pearson similarity, a cosine similarity, and so on. The training ends when all the feature vectors have been added to a cluster. The cluster containing feature vectors for the AF ECGs, the VF ECGs, and neither are identified, and the corresponding classification is associated with each cluster. To classify an ECG, a feature vector is generated based on the ECG, the cluster with a mean that is most similar to that feature vector is identified, and the ECG is assigned the classification of that cluster.

A generative adversarial network (GAN) or an attribute (attGAN) may also be used. (See Zhenliang He, Wangmeng Zuo, Meina Kan, Shiguang Shan, and Xilin Chen, "AttGAN: Facial Attribute Editing by Only Changing What You Want," IEEE Transactions on Image Processing, vol. 28, No. 11, pp. 5464-5478, November 2019; and Ian Goodfellow, Jean Pouget-Abadie, Mehdi Mirza, Bing Xu, David Warde-Farley, Sherjil Ozair, Aaron Courville, and Yoshua Bengio, "Generative Adversarial Nets," Advances in Neural Information Processing Systems 27, pp. 2672-2680, 2014, which are hereby incorporated by reference.) A GAN employs a generator and discriminator and is trained using training data such as real images of objects. The generator generates generated images based on random input. The generator is trained to generate generated images that cannot be distinguished from real images. The discriminator indicates whether an input image is real or generated. The generator and discriminator are trained in parallel to learn weights. The generator is trained to generate increasingly more realistic images, and the discriminator is trained to discriminate between real images and generated images more effectively. After being trained, the C&I system may employ the discriminator to discriminate between real images and generated (fake) images. For example, the real images may be AF ECGs for an AF ML model and VF ECGs for a VF ML model.

Transformer machine learning was introduced as an alternative to a recurrent neural network that is both more effective and more parallelizable. (See Vaswani, Ashish, et al., "Attention is all you need," Advances in Neural Information Processing Systems 30, 2017, which is hereby incorporated by reference.) Transformer machine learning was originally described in the context of natural language processing (NLP) but has been adapted to other applications, such as image processing to augment or replace a CNN. In the following, transformer machine learning is described in the context of NLP as introduced by Vaswani.

A transformer includes an encoder whose output is input to a decoder. The encoder includes an input embedding layer followed by one or more encoder attention layers. The input embedding layer generates an embedding of the inputs. For example, if a transformer ML model is used to process a sentence as described by Vaswani, each word may be represented as a token that includes an embedding of a word and its positional information. Such an embedding is a vector representation of a word, such that words with similar meanings are closer in the vector space. The positional information is based on position of the word in the sentence.

The first encoder attention layer inputs the embeddings and the other encoder attention layers input the output from the prior encoder attention layer. An encoder attention layer includes a multi-head attention mechanism followed by a normalization sublayer whose output is input to a feedforward neural network followed by a normalization sublayer. A multi-head attention mechanism includes multiple self-attention mechanisms that each input the encodings of the previous layer and weigh the relevance encodings to other encodings. For example, the relevance may be determined by the following attention function:

$$\text{Attention}(Q, K, V) = \text{softmax}\left(\frac{QK^T}{\sqrt{d_k}}\right)V$$

where Q represents a query, K represents a key, V represents a value, and $d_k$ represents the dimensionality of K. This attention function is referred to as scaled dot-product attention. In Vaswani, the query, key, and value of an encoder multi-head attention mechanism are set to the input of the encoder attention layer. The multi-head attention mechanism determines the multi-head attention as represented by the following:

$$\text{MultiHead}(Q, K, V) = \text{concat}(\text{head}_1, \ldots, \text{head}_8)W^o$$

$$\text{head}_i = \text{Attention}(QW_i^Q, KW_i^K, VW_i^V)$$

where W represents weights that are learned during training. The weights for the feedforward networks are also learned during training. The weights may be initialized to random values. A normalization layer normalizes its input to a vector having a dimension as expected by the next layer or sublayer.

The decoder includes an output embedding layer, a decoder attention layer, a linear layer, and a softmax layer. The output embedding layer inputs the output of the decoder shifted right. Each decoder attention layer inputs the output of the prior decoder attention layer (or the output embedding layer) and the output of the encoder. The output of the output embedding layer is input to the decoder attention layer, the output of the decoder attention layer is input to the linear layer, and the output of the linear layer is input to the softmax layer, which outputs probabilities. A decoder attention layer includes a decoder masked multi-head attention mechanism followed by a normalization sublayer, a decoder multi-head attention mechanism followed by a normalization sublayer, and a feedforward neural network followed by a normalization sublayer. The decoder masked multi-head attention mechanism masks the input so that predictions for a position are based only on outputs for prior positions. A decoder multi-head attention mechanism inputs the normalized output of the decoder masked multi-head attention mechanism as a query and the output of the encoder as a key and a value. The feedforward neural network inputs the normalized output of the decoder multi-head attention mechanism. The normalized output of the feedforward neural network is the output of that multi-head attention layer. The weights of the linear layer are also learned during training.

Although initially developed to process sentences, transformers have been adapted for image recognition. The input to such a transformer may be a representation of fixed-size patches of the image. The representation of a patch may be, for each pixel of the patch, an encoding of its row, column, and color. The output of the transformer may be, for example, a classification of the image.

The features used by an ML model may be manually or automatically selected. Features that an assessment indicates may be useful in providing an accurate output for an ML model are referred to as informative features. The assessment of which features are informative may be based on various feature selection techniques such as a predictive power score, a lasso regression, a mutual information analysis, and so on.

Figure 3:
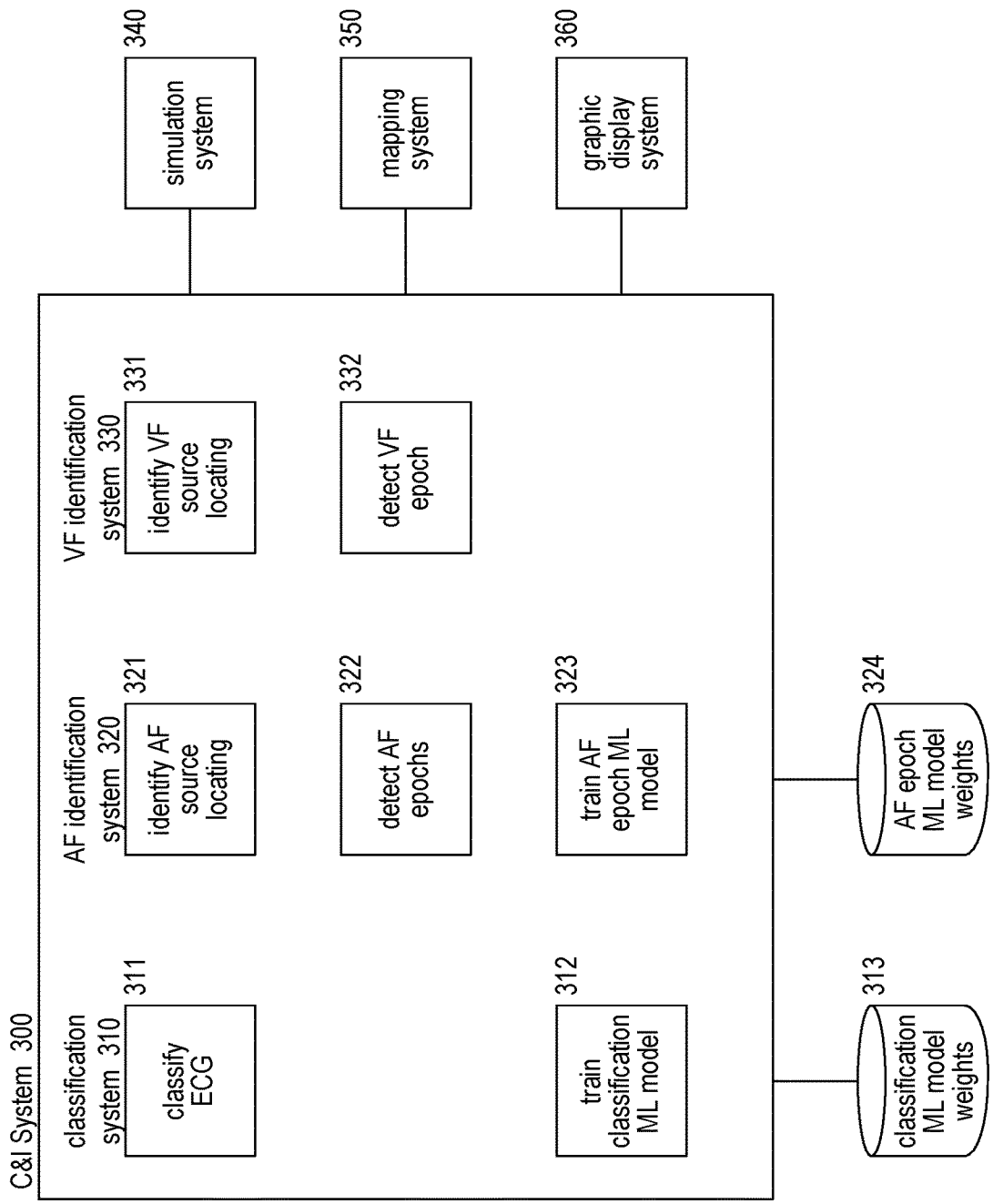
FIG. 3 is a block diagram that illustrates components of the classification and identification system in some embodiments.

FIG. 3 is a block diagram that illustrates components of the classification and identification system in some embodiments. The C&I system 300 includes a classification system 310, an AF identification system 320, and a VF identification system 330. The classification system includes a classify ECG component 311, a train classification ML model component 312, and a classification ML model weights data store 313. The AF identification system includes an identify AF source locations component 321, a detect AF epochs component 322, a train AF epoch ML model component 323, and an AF epoch ML model weights data store 324. The VF identification system includes an identify VF source locations component 331 and a detect VF epoch component 332. The C&I system interfaces with a simulation system 340, a mapping system 350, and a graphic display system 360. The classify ECG component receives an ECG and classifies it as an AF or a VF ECG. The identify AF source locations component is provided an AF ECG and identifies source locations associated with the AF ECG. The detect AF epochs component is passed an AF ECG and identifies AF epochs within the AF ECG. The identify VF source locations component is passed a VF ECG and identifies one or more source locations for the VF ECG. The detect VF epoch component identifies the VF epoch of the VF ECG. The train classification ML model component trains a classification ML model and stores the weights in the classification ML model weights data store. The train AF epoch ML model component trains an AF epoch ML model and stores the weights in the AF epoch ML model weights data store. The simulation system and mapping systems may be systems as described in U.S. Pat. No. 10,860,754. The graphic display system may be the system as described in U.S. Pub. No. 2022-0133207.

Figure 4:
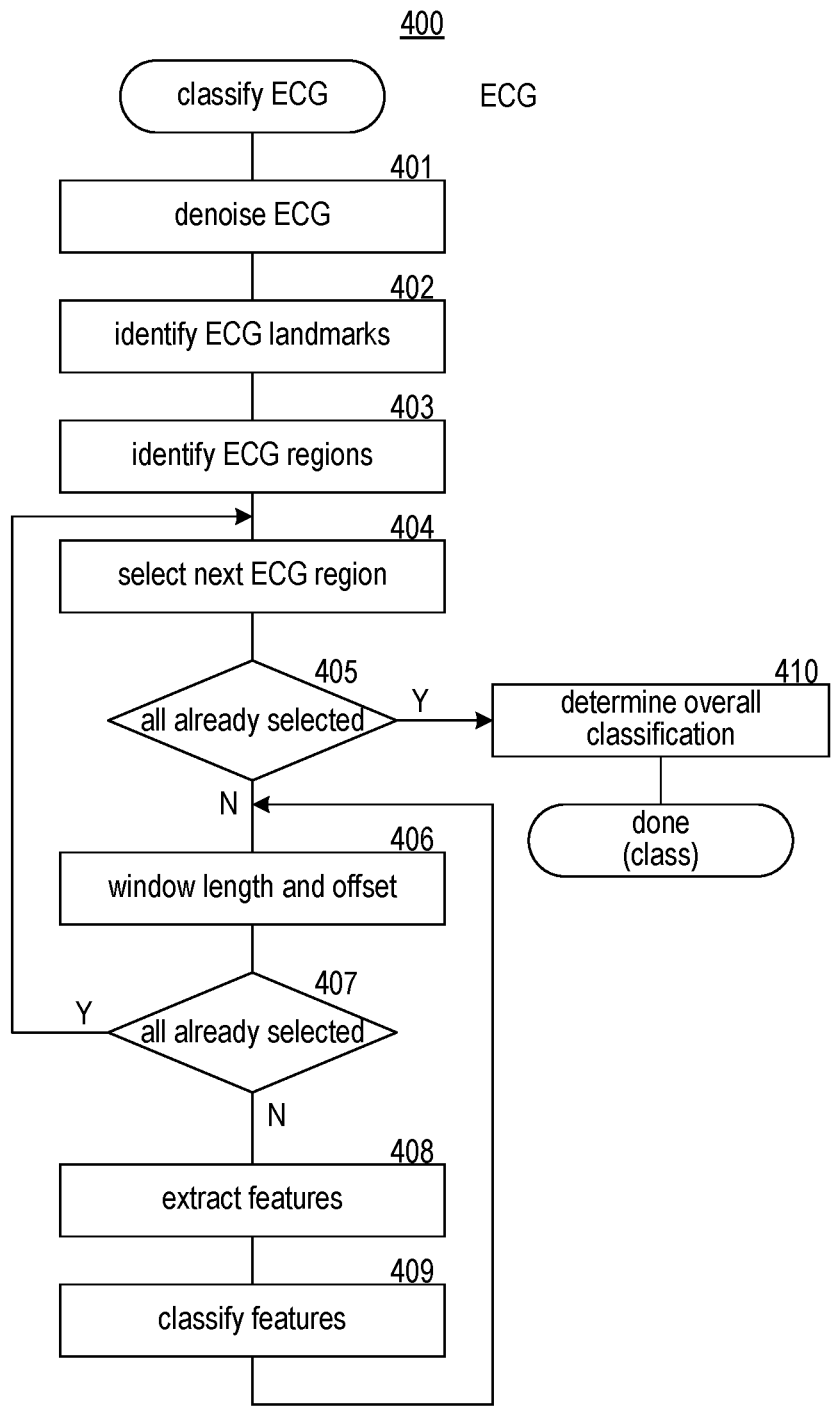
FIG. 4 is a flow diagram that illustrates the processing of a classify ECG component in some embodiments.

FIG. 4 is a flow diagram that illustrates the processing of a classify ECG component in some embodiments. The classify ECG component 400 is passed an ECG and classifies the ECG as being an AF ECG or a VF ECG. In block 401, the component denoises the ECG. In block 402, the component identifies ECG landmarks within the ECG. In block 403, the component identifies an ECG regions in the ECG based on the ECG landmarks. In block 404, the component selects the next ECG region. In decision block 405, if all the ECG regions have already been selected, then the component continues at block 410, else the component continues at block 406. In block 406, the component selects a window length and an offset from the beginning of the ECG region. In decision block 407, if all the combinations of window length and offset have already been selected, then the component loops to block 404, else the component continues at block 408. In block 408, the component extracts features from the window. In block 409, the component generates a classification of the features as representing an AF or VF (by applying a classification ML model) and then loops to block 406 to select the next window length and offset. In block 410, the component determines an overall classification for the ECG and completes.

Figure 5:
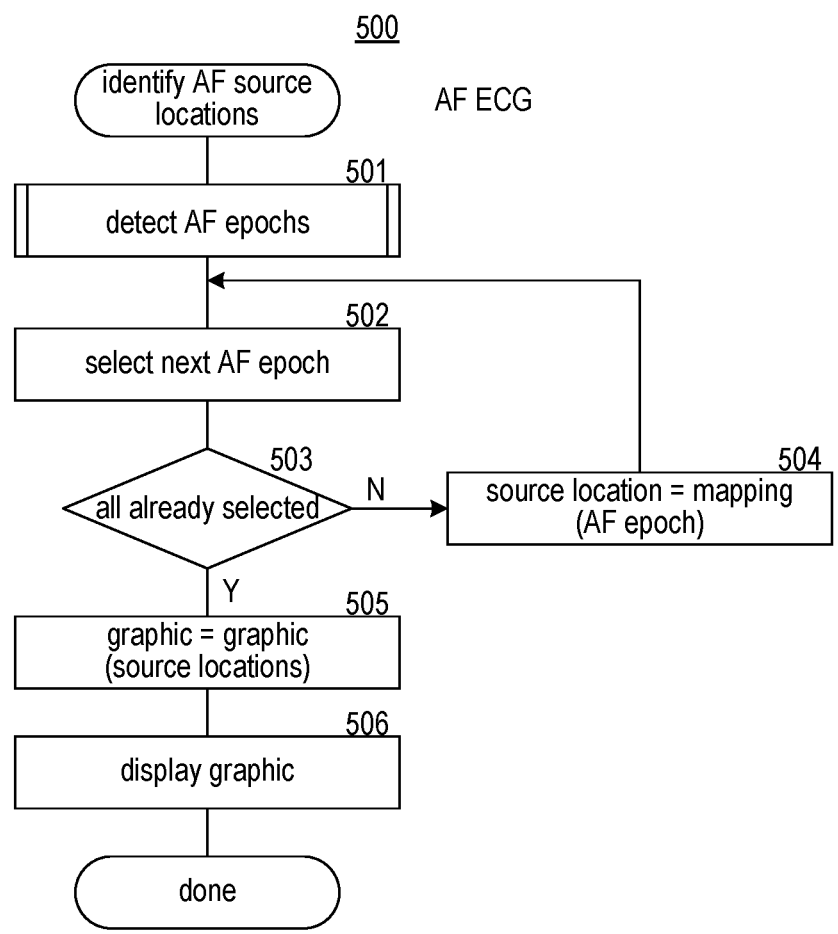
FIG. 5 is a flow diagram that illustrates the processing of an identify AF source locations component in some embodiments.

FIG. 5 is a flow diagram that illustrates the processing of an identify AF source locations component in some embodiments. The identify AF source locations component 500 is passed an AF ECG and identifies one or more source locations. In block 501, the component invokes a detect AF epochs component to identify the AF epochs within the AF ECG. In block 502, the component selects the next AF epoch. In decision block 503, if all the AF epochs have already been selected, then the component continues at block 505, else the component continues at block 504. In block 504, the component employs a mapping system to identify a source location associated with the AF epoch and then loops to block 502 to select the next AF epoch. In block 505, the component employs a graphic system to generate a graphic of the heart with the source locations indicated. In block 506, the component displays the graphic and then completes.

Figure 6:
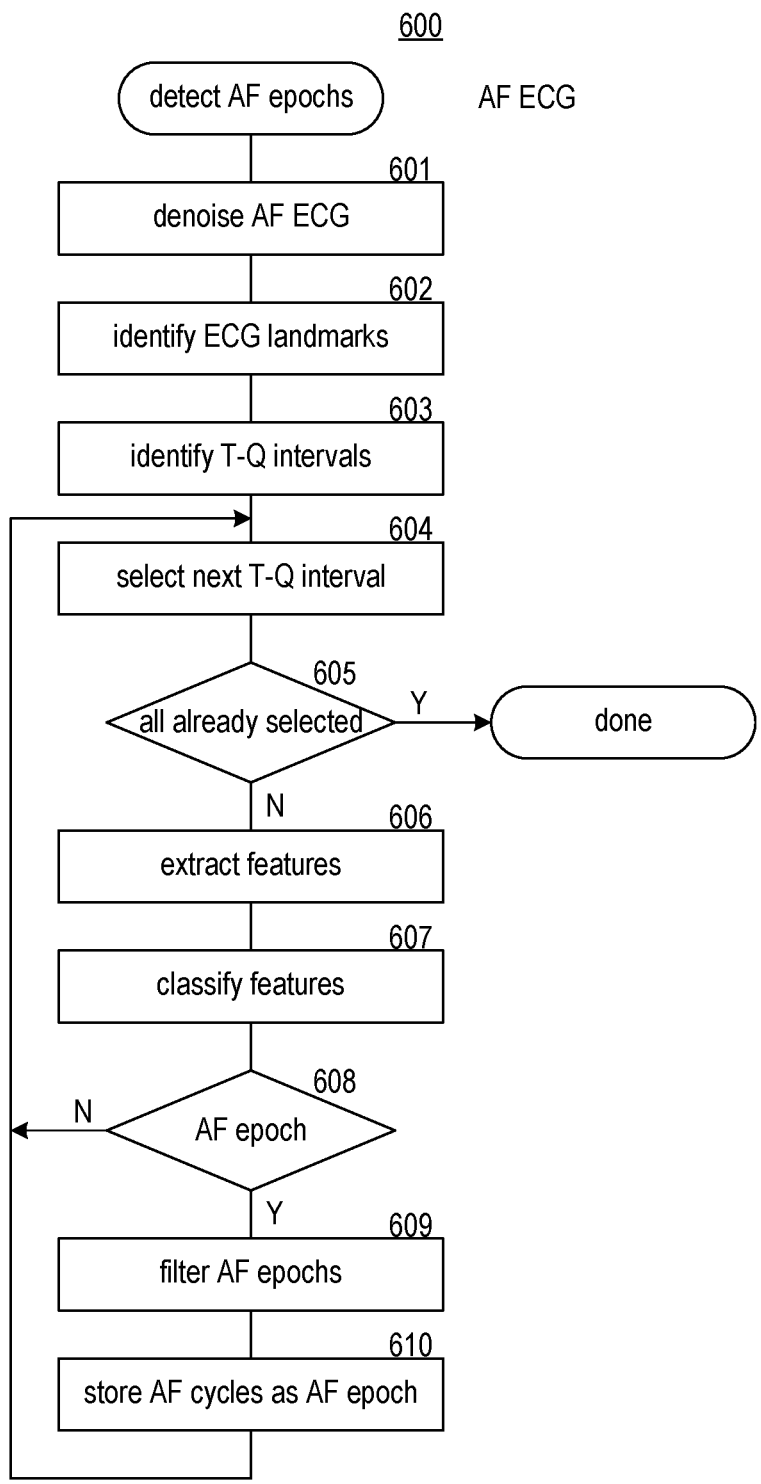
FIG. 6 is a flow diagram that illustrates the processing of a detect AF epochs component in some embodiments.

FIG. 6 is a flow diagram that illustrates the processing of a detect AF epochs component in some embodiments. The detect AF epochs component 600 is passed an AF ECG and identifies the AF epochs within the AF ECG. In block 601, the component denoises the AF ECG. In block 602, the component identifies ECG landmarks within the AF ECG. In block 603, the component identifies T-Q intervals based on the ECG landmarks. In block 604, the component selects the next T-Q interval. In decision block 605, if all the T-Q intervals have been selected, then the component completes, else the component continues at block 606. In block 606, the component extracts features. In block 607, the component employs an AF epoch ML model to classify the T-Q interval as being an AF epoch or a non-AF epoch. In decision block 608, if the T-Q interval is classified as an AF epoch, then the component continues at block 609, else the component loops to block 604 to select the next T-Q interval. In block 609, the component filters the AF epoch to remove AF cycles that do not satisfy an AF cycle criterion. In block 610, the component stores the remaining (filtered) AF cycles as an AF epoch and then loops to block 604 to select the next T-Q interval.

Figure 7:
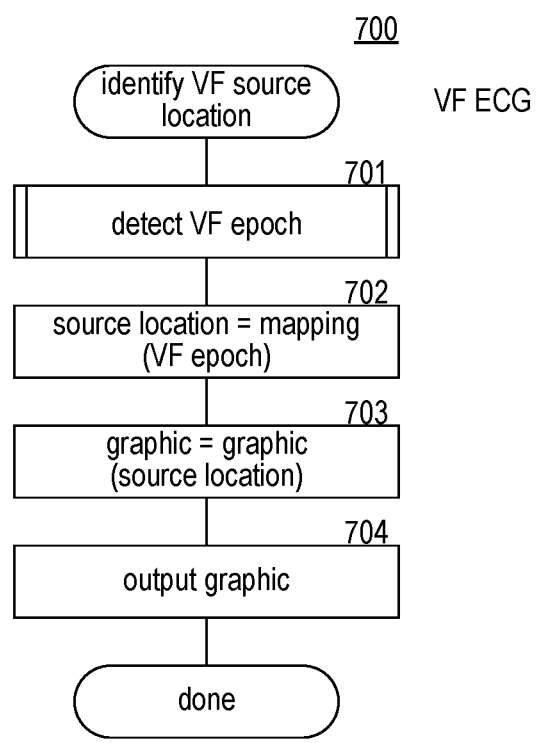
FIG. 7 is a flow diagram that illustrates the processing of an identify VF source locations component in some embodiments.

FIG. 7 is a flow diagram that illustrates the processing of an identify VF source locations component in some embodiments. The identify VF source locations component 700 inputs a VF ECG and identifies a source location associated with that VF ECG. In block 701, the component invokes a detect VF epoch component to identify the VF epoch within the VF ECG. In block 702, the component employs the mapping system to identify the source location associated with the VF epoch. The component may also identify source locations for various subsets of the combinations of the VF cycles of the VF epoch. In block 703, the component employs a graphics system to generate a graphic based on the source location(s). In block 704, the component outputs the graphic and then completes.

Figure 8:
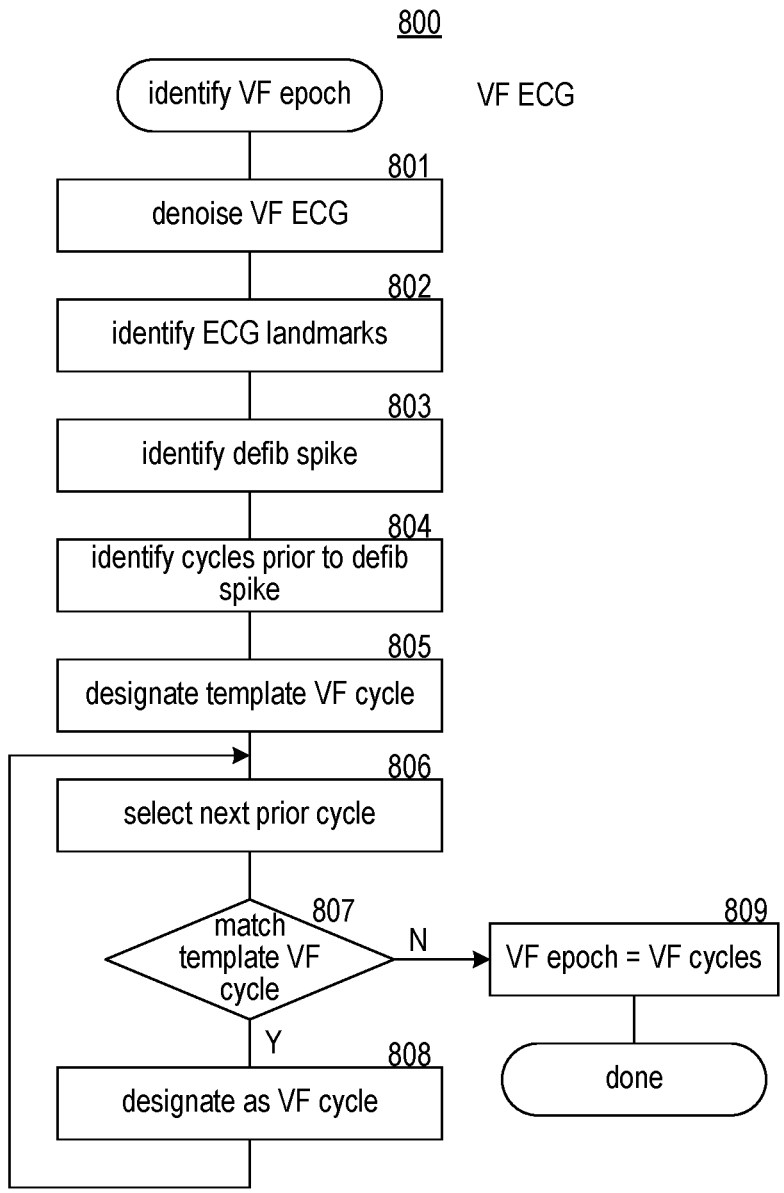
FIG. 8 is a flow diagram that illustrates the processing of a detect VF epoch component in some embodiments.

FIG. 8 is a flow diagram that illustrates the processing of a detect VF epoch component in some embodiments. The detect VF epoch component 800 is passed a VF ECG and identifies a VF epoch within the VF ECG. In block 801, the component denoises the VF ECG. In block 802, the component identifies ECG landmarks within the VF ECG. In block 803, the component identifies a defibrillation spike within the VF ECG. In block 804, the component identifies cycles that are prior to the identified defibrillation spike. In block 805, the component designates a template VF cycle based on one or more of the identified cycles that are within a template range before the defibrillation spike. In block 806, the component selects the next prior cycle that is before the previously identified VF cycles. In decision block 807, if the prior cycle matches the template VF cycle or other VF cycle criterion, then the component continues at block 808, else the component continues at block 809. In block 808, the component designates the prior cycle as a VF cycle and loops to block 806 to select the next prior cycle. In block 809, the component specifies the VF cycles as composing the VF epoch and then completes.

The following paragraphs describe various aspects of the C&I system. An implementation of the system may employ any combination of the aspects. The processing described below may be performed by a computing system with a processor that executes computer-executable instructions stored on a computer-readable storage medium that implements the system.

In some aspects, the techniques described herein relate to one or more computing systems for identifying an atrial fibrillation (AF) epoch of a patient based at least on a patient cardiogram collected from a patient, the one or more computing systems including: one or more computer-readable storage mediums that store: training T-Q intervals of cardiograms that are AF epochs or not AF epochs; and computer-executable instructions for controlling the one or more computing systems to: generate training data that includes, for each of a plurality of the training T-Q intervals, a feature vector derived from that training T-Q interval that is labeled as an AF epoch or not an AF epoch; train an AF epoch machine learning (ML) model using the generated training data; apply an AF epoch ML model to the patient cardiogram to determine whether the patient cardiogram is an AF cardiogram; identify one or more landmarks within the patient cardiogram; identify a T-Q interval within the patient cardiogram based on the identified one or more landmarks; apply the AF epoch ML model to a feature vector derived from the identified T-Q interval to determine whether the identified T-Q interval represents an AF epoch; and output an indication of the determination; and one or more processors for controlling the one or more computing systems to execute one or more of the computer-executable instructions.

In some aspects, the techniques described herein relate to one or more computing systems wherein the computer-executable instructions further include instructions that: apply a mapping system to the identified T-Q interval to identify a source location of the AF represented by the AF epoch; and display a graphic of a heart that illustrates the source location of the AF.

In some aspects, the techniques described herein relate to one or more computing systems wherein the computer-executable instructions that identify one or more landmarks identify one or more T peaks and Q peaks.

In some aspects, the techniques described herein relate to one or more computing systems wherein the training T-Q intervals include simulated training T-Q intervals generated based on simulations of electric activity of hearts having different characteristics.

In some aspects, the techniques described herein relate to one or more computing systems wherein the training T-Q intervals include clinical training T-Q intervals collected from patients.

In some aspects, the techniques described herein relate to one or more computing systems wherein the computer-executable instructions further include instructions to identify AF cycles within an AF epoch and filter out one or more AF cycles that do not satisfy an AF cycle criterion.

In some aspects, the techniques described herein relate to one or more computing systems wherein the computer-executable instructions further include instructions that: apply a mapping system to the identified T-Q interval to identify a source location of the AF; and output the source location of the AF to an ablation therapy device.

In some aspects, the techniques described herein relate to one or more computing systems wherein the feature vector includes an image of a T-Q interval and the AF epoch ML model includes a convolutional neural network.

In some aspects, the techniques described herein relate to one or more computing systems wherein the AF epoch ML model includes a transformer.

In some aspects, the techniques described herein relate to one or more computing systems wherein the feature vector includes an image of a T-Q interval and the AF epoch ML model includes a generative adversarial network.

In some aspects, the techniques described herein relate to one or more computing systems wherein the feature vector includes a voltage-time series representation of a T-Q interval and the AF epoch ML model includes a recurrent neural network.

In some aspects, the techniques described herein relate to one or more computing systems for identifying a ventricular fibrillation (VF) epoch of a patient based at least on a patient cardiogram collected from a patient, the one or more computing systems including: one or more computer-readable storage mediums that store computer-executable instructions for controlling the one or more computing systems to: identify a defibrillation spike within the patient cardiogram based on characteristics of a defibrillation spike; identify one or more VF cycles prior to the defibrillation spike; designate a template VF cycle based on the one or more of the identified VF cycles; identify a sequence of VF cycles that are similar to the template VF cycle based on satisfying a similarity criterion; designate the identified sequence of VF cycles as a VF epoch; and output an indication of the VF epoch; and one or more processors for controlling the one or more computing systems to execute one or more of the computer-executable instructions. In some aspects, the techniques described herein relate to one or more computing systems wherein the computer-executable instructions further include instructions to: apply a mapping system to the VF epoch to identify a source location of the VF; and display a graphic of a heart that illustrates the source location of the VF. In some aspects, the techniques described herein relate to one or more computing systems wherein the computer-executable instructions further include instructions to provide the source location to an ablation therapy device. In some aspects, the techniques described herein relate to one or more computing systems wherein the computer-executable instructions further include instructions to: access training defibrillation spikes of cardiograms and training non-defibrillation spike portions of cardiograms; generate training data that includes, for each training defibrillation spike, a feature vector derived from that training defibrillation spike that is labeled as a defibrillation spike; generate training data that includes, for each training non-defibrillation spike portion, a feature vector derived from that training non-defibrillation spike portion that is labeled as a non-defibrillation spike portion; and train a defibrillation spike machine learning (ML) model using the generated training data. In some aspects, the techniques described herein relate to one or more computing systems wherein the feature vector includes an image of a defibrillation spike or a non-defibrillation spike portion and the defibrillation spike ML model includes a convolutional neural network. In some aspects, the techniques described herein relate to one or more computing systems wherein the feature vector includes a voltage-time series representation of a defibrillation spike or a non-defibrillation spike portion and the defibrillation spike ML model includes a recurrent neural network. In some aspects, the techniques described herein relate to one or more computing systems wherein the defibrillation spike ML model is used to identify the defibrillation spike. In some aspects, the techniques described herein relate to one or more computing systems wherein a match filter is used to identify the defibrillation spike.

In some aspects, the techniques described herein relate to a method performed by one or more computing systems for identifying a source location of an atrial fibrillation (AF), the method including: receiving a patient AF cardiogram collected from a patient; identifying a T-Q interval of the patient AF cardiogram; applying a machine learning (ML) model to a T-Q interval to determine whether the T-Q interval is an AF epoch; applying a mapping system to the AF epoch to identify the source location of the AF; and outputting an indication of the source location to inform treatment of the patient. In some aspects, the techniques described herein relate to a method further including generating a graphic that includes a heart with the source location demarcated. In some aspects, the techniques described herein relate to a method further including providing the source location to an ablation therapy device. In some aspects, the techniques described herein relate to a method wherein the mapping system is a cloud-based computing system and wherein the applying includes sending an indication of the AF epoch to the mapping system and receiving the source location from the mapping system.

In some aspects, the techniques described herein relate to a method performed by one or more computing systems for identifying a source location of a ventricular fibrillation (VF), the method including: receiving a patient VF cardiogram collected from a patient; identifying an end of a VF epoch within the patient VF cardiogram based on presence of a defibrillation spike within the patient VF cardiogram; identifying a start of the VF epoch; applying a mapping system to the VF epoch to identify the source location of the VF; and outputting an indication of the source location to inform treatment of the patient. In some aspects, the techniques described herein relate to a method further including generating a graphic that includes a heart with the source location demarcated. In some aspects, the techniques described herein relate to a method further including providing the source location to an ablation therapy device. In some aspects, the techniques described herein relate to a method wherein the end of the VF epoch is identified using a defibrillation spike machine learning (ML) model. In some aspects, the techniques described herein relate to a method wherein the identification of the end and the start of the VF epoch is based on a VF epoch machine learning (ML) model trained using VF cardiograms that are each labeled with an indication of a VF epoch within the VF cardiogram. In some aspects, the techniques described herein relate to a method wherein the mapping system is a cloud-based computing system and wherein the applying includes sending an indication of the VF epoch to the mapping system and receiving the source location from the mapping system.

In some aspects, the techniques described herein relate to a method performed by one or more computing systems for classifying a cardiogram as an atrial fibrillation (AF) cardiogram or a ventricular fibrillation (VF) cardiogram, the method including: receiving a patient cardiogram collected from a patient; identifying cardiogram landmarks within the patient cardiogram; identifying cardiogram regions based on the cardiogram landmarks; for each of the cardiogram regions, for each of a plurality of windows with different lengths or different offsets from a start of the cardiogram region, applying a machine learning (ML) model to features derived from the window to classify the window as an AF region, a VF region, or another region; and determining a classification for the patient cardiogram based on the classifications of the windows. In some aspects, the techniques described herein relate to a method wherein the ML model is a convolutional neural network. In some aspects, the techniques described herein relate to a method wherein the ML model includes an AF ML model to classify a cardiogram as an AF or not an AF and a VF ML model to classify a cardiogram as a VF or not a VF. In some aspects, the techniques described herein relate to a method wherein the AF ML model and the VF ML model are transformers. In some aspects, the techniques described herein relate to a method wherein the AF ML model and the VF ML model are generative adversarial networks.

All documents incorporated by reference are incorporated in their entirety for the full extent of their disclosures. In the event of inconsistencies between the language in this document and any incorporated-by-reference document, the language in the incorporated-by-reference document should be considered supplementary to that of this document, and the language in this document controls.

Although the subject matter has been described in language specific to structural features and/or acts, it is to be understood that the subject matter defined in the appended claims is not necessarily limited to the specific features or acts described above. Rather, the specific features and acts described above are disclosed as example forms of implementing the claims.

We claim:

1. One or more computing systems for identifying an atrial fibrillation (AF) epoch of a patient based at least on a patient cardiogram collected from a patient, the one or more computing systems comprising:
   one or more computer-readable storage mediums that store:
      training T-Q intervals of cardiograms that are AF epochs or not AF epochs; and
      computer-executable instructions for controlling the one or more computing systems to:
         generate training data that includes, for each of a plurality of the training T-Q intervals, a feature vector derived from that training T-Q interval that is labeled as an AF epoch or not an AF epoch;
         train an AF epoch machine learning (ML) model using the generated training data, the AF epoch ML model being a neural network having connected layers with activation functions having weights, wherein the AF epoch ML model is trained to learn weights of the activation functions that tend to minimize a loss function;

apply an AF classification ML model to the patient cardiogram to determine whether the patient cardiogram is an AF cardiogram; and when the patient cardiogram is an AF cardiogram,
identify one or more landmarks within the patient cardiogram;
identify a T-Q interval within the patient cardiogram based on the identified one or more landmarks;
apply the AF epoch ML model to a feature vector derived from the identified T-Q interval to determine whether the identified T-Q interval represents an AF epoch;
apply a mapping system to the identified T-Q interval to identify a source location of the AF;
output the source location of the AF to an ablation therapy device; and
direct the ablation therapy device to perform an ablation targeting the source location; and one or more processors for controlling the one or more computing systems to execute one or more of the computer-executable instructions.

2. The one or more computing systems of claim 1 wherein the computer-executable instructions further include instructions that:
display a graphic of a heart that illustrates the source location of the AF.

3. The one or more computing systems of claim 1 wherein the computer-executable instructions that identify one or more landmarks identify one or more T peaks and Q peaks.

4. The one or more computing systems of claim 1 wherein the training T-Q intervals include simulated training T-Q intervals generated based on simulations of electric activity of hearts having different characteristics.

5. The one or more computing systems of claim 1 wherein the training T-Q intervals include clinical training T-Q intervals collected from patients.

6. The one or more computing systems of claim 1 wherein the computer-executable instructions further comprise instructions to identify AF cycles within an AF epoch and filter out one or more AF cycles that do not satisfy an AF cycle criterion.

7. The one or more computing systems of claim 1 wherein the feature vector includes an image of a T-Q interval and the AF epoch ML model includes a convolutional neural network.

8. The one or more computing systems of claim 1 wherein the AF epoch ML model includes a transformer.

9. The one or more computing systems of claim 1 wherein the feature vector includes an image of a T-Q interval and the AF epoch ML model includes a generative adversarial network.

10. The one or more computing systems of claim 1 wherein the feature vector includes a voltage-time series representation of a T-Q interval and the AF epoch ML model includes a recurrent neural network.

11. A method for treating a patient, the method comprising:
performing by one or more computing systems identification of an atrial fibrillation (AF) epoch of the patient, the method comprising:
accessing a patient cardiogram collected from the patient;
applying an AF classification machine learning (ML) model to the patient cardiogram to determine whether the patient cardiogram is an AF cardiogram, the AF classification ML model being a neural network that is trained using classification training data that includes feature vectors representing one or more features of training cardiograms and labels indicating whether the training cardiograms are AF cardiograms; and
when the patient cardiogram is an AF cardiogram,
identifying one or more landmarks within the patient cardiogram;
identifying a T-Q interval within the patient cardiogram based on the identified one or more landmarks; and
applying an AF epoch ML model to a feature vector with one or more features derived from the identified T-Q interval to determine whether the identified T-Q interval represents an AF epoch, the AF epoch ML model trained using training data that includes, for each of a plurality of the training T-Q intervals, a feature vector derived from that training T-Q interval that is labeled as an AF epoch or not an AF epoch; and
performing an ablation on the patient based on the determination that the identified T-Q interval represents an AF epoch.

12. The method of claim 11 further comprising training the AF epoch ML model using the epoch training data.

13. The method of claim 11 further comprising when the identified T-Q interval represents an AF epoch,
applying a mapping system to the identified T-Q interval to identify a source location of the AF represented by the AF epoch; and
displaying a graphic of a heart that illustrates the source location of the AF.

14. The method of claim 11 further comprising when the identified T-Q interval represents an AF epoch,
applying a mapping system to the identified T-Q interval to identify a source location of the AF represented by the AF epoch; and
outputting the source location of the AF to an ablation therapy device to control the performing of the ablation targeting the source location.

15. A method for treating a target patient, the method comprising:
performing by one or more computing system for training of an atrial fibrillation (AF) epoch machine learning (ML) model, the method comprising:
accessing a plurality of training T-Q intervals along with indications of whether the training T-Q intervals represent an AF epoch or not an AF epoch;
for each training T-Q interval, generating training data that includes a feature vector with one or more features derived from that training T-Q interval and a label indicating whether that training T-Q interval represents an AF epoch or not an AF epoch;
training the AF epoch ML model that is a neural network using the training data wherein the AF epoch ML model inputs a feature vector with one or more features derived from a T-Q interval of a patient cardiogram and outputs an indication of whether the T-Q interval represents an AF epoch; and
inputting to the trained AF epoch ML model features derived from a target patient T-Q interval of a target patient cardiogram of the target patient wherein the trained AF epoch ML model outputs an indication of whether the target patient T-Q interval represents an AF each; and performing an ablation on the target patient based on the target patient T-Q interval representing an AF epoch.

16. The method of claim 15 further comprising identifying a training T-Q intervals from a training cardiogram by identifying one or more landmarks that include one or more T peaks and one or more Q peaks.

17. The method of claim 15 wherein the training T-Q intervals include simulated training T-Q intervals generated based on simulations of electric activity of hearts having different characteristics and/or clinical training T-Q intervals collected from patients.

18. The method of claim 15 wherein the feature vector includes an image of a T-Q interval and the AF epoch ML model includes a convolutional neural network.

19. The method of claim 15 wherein the AF epoch ML model includes a transformer.

20. The method of claim 15 wherein the feature vector includes an image of a T-Q interval and the AF epoch ML model includes a generative adversarial network.

21. The method of claim 15 wherein the feature vector includes a voltage-time series representation of a T-Q interval and the AF epoch ML model includes a recurrent neural network.

22. The method of claim 15 wherein a feature vector includes a feature that is an image of a T-Q interval and the AF epoch ML model includes a convolutional neural network.

23. One or more computing systems for identifying an atrial fibrillation (AF) epoch of a patient cardiogram collected from a patient, the one or more computing systems comprising:

one or more computer-readable storage mediums that store computer-executable instructions for controlling the one or more computing systems to:

receive patient cardiogram that was collected from the patient, the patient cardiogram representing an AF cardiogram;

identify one or more landmarks within the patient cardiogram;

identify a T-Q interval within the patient cardiogram based on the identified one or more landmarks;

apply an AF epoch machine learning (ML) model to a feature vector with one or more features derived from the identified T-Q interval to determine whether the identified T-Q interval represents an AF epoch, the AF epoch ML model trained using training data that includes, for each of a plurality of the training T-Q intervals, a feature vector derived from that training T-Q interval that is labeled as an AF epoch or not an AF epoch; and apply a mapping system to the identified T-Q interval to identify a source location of the AF;

control an ablation therapy device to perform an ablation targeting the source location; and one or more processors for controlling the one or more computing systems to execute one or more of the computer-executable instructions.

24. The one or more computing systems of claim 23 wherein the one or more of the computing systems is a cloud-based system and the patient cardiogram is received from a client-side computing system and the indication of the determination is output to the client-side computing system.

25. The one or more computing systems of claim 23 wherein the computer-executable instruction include computer-executable instructions that control the one or more computing systems to train the AF epoch ML model using the training data.

26. The one or more computing systems of claim 23 wherein the computer-executable instruction include computer-executable instructions that control the one or more computing systems to apply a mapping system to the identified T-Q interval to identify a source location of the AF represented by the AF epoch and to display a graphic of a heart that illustrates the source location of the AF.

27. The one or more computing systems of claim 23 wherein the AF epoch ML model includes a transformer.

28. The one or more computing systems of claim 23 wherein a feature vector a feature that is an image of a T-Q interval and the AF epoch ML model includes a generative adversarial network.

* * * * *